United States Patent [19]

Smolikowski et al.

[11]  4,181,735
[45]  Jan. 1, 1980

[54] NEMATOCIDAL CYCLOPROPANE CARBOXYLATES

[75] Inventors: Serge Smolikowski, Marseille; Jean J. Herve, Aubagne, both of France

[73] Assignee: Roussel UCLAF, Paris, France

[21] Appl. No.: 937,990

[22] Filed: Aug. 30, 1978

[30] Foreign Application Priority Data

Sep. 8, 1977 [FR] France ............................... 77 27191

[51] Int. Cl.² .......................... A01N 9/06; A01N 9/20
[52] U.S. Cl. .................................................. 424/304
[58] Field of Search ......................................... 424/304

[56] References Cited

U.S. PATENT DOCUMENTS

| | | | |
|---|---|---|---|
| 3,835,176 | 9/1974 | Matsuo et al. | 260/465 D |
| 4,136,195 | 1/1979 | Warnant et al. | 424/304 |

OTHER PUBLICATIONS

Chemical Abstracts, 85:186823d (1976).

*Primary Examiner*—Leonard Schenkman

*Attorney, Agent, or Firm*—Hammond & Littell

[57] ABSTRACT

Novel compositions for the control of acariens and parasitic nematodes of vegetables having as the active component a compound of the formula

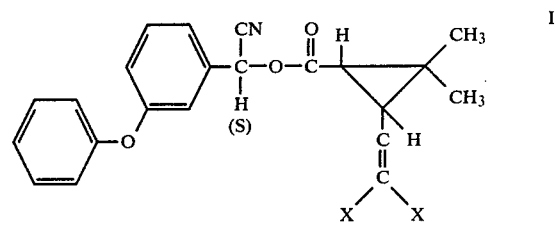

wherein X is selected from the group consisting of chlorine and bromine and the alcohol is the (S) structure and the acid has the cis or trans, racemic or optically active form and to a method of combatting acariens and nematodes.

3 Claims, No Drawings

NEMATOCIDAL CYCLOPROPANE CARBOXYLATES

STATE OF THE ART

The compounds of formula I are known to possess insecticidal activity and French Pat. No. 2,300,553 describes (R,S) α-cyano-3-phenoxy-benzyl 2,2-dimethyl-3-(2',2'-dichlorovinyl)-cyclopropane-1-carboxylate and its use to control animal parasitic acariens.

OBJECTS OF THE INVENTION

It is an object of the invention to provide novel acaricidal and nematocidal compositions and to provide a novel method of combatting nematodes and acariens in plants.

These and other objects and advantages of the invention will become obvious from the following detailed description.

THE INVENTION

The novel agricultural acaricidal and nematocidal compositions of the invention are comprised of an acaricidally and nematocidally effect amount of at least one compound of the formula

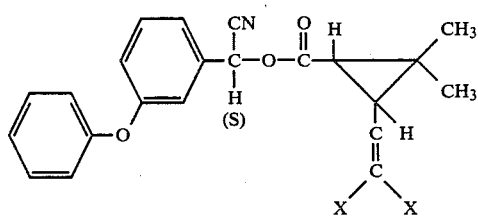

wherein X is selected from the group consisting of chlorine and bromine and the alcohol is the (S) structure and the acid has the cis or trans, racemic or optically active form and an inert carrier. The preferred compounds of formula I are (S) α-cyano-3-phenoxy-benzyl 1R,cis 2,2-dimethyl-3-(2',2'-dichlorovinyl)-cyclopropane-1-carboxylate and (S) α-cyano-3- phenoxy-benzyl 1R,cis 2,2-dimethyl-3-(2',2'-dibromovinyl)-cyclopropane-1-carboxylate.

The compounds of formula I have been found to be useful in the agricultural field for the control of parasitic acariens of vines and fruit trees such as Panonychus ulmi and Eotetranychus carpini as well as for the control of nematodes of the meloidoigenic family such as Ditylenchus Myceliophagus in vegetable crops.

The compositions may also contain one or more other pesticidal agents and may be in the form of powders, granules, suspensions, emulsions, solutions or other preparations commonly used for these types of preparations. The compositions may generally contain besides the compounds of formula I a vehicle and/or a nonionic surface active agent to ensure a uniform dispersion of the ingredients of the composition. Examples of suitable vehicles are liquids such as water, alcohol, hydrocarbons or other organic solvents, a mineral, animal or vegetable oil or a powder such as talc, clays, silicates and kieselguhr.

The preferred acaricidal compositions of the invention are powders or liquids for foliar spraying containing 20 to 80% by weight of the active material and powders for foliage powdering containing 1 to 5% by weight of the active material. The preferred nematocidal compositions of the invention are in the form of powders or liquids for treating the soil containing 40 to 90% by weight of the active material.

The novel method of the invention for combatting plant acariens or nematodes comprises contacting the acariens or nematodes with a lethal amount of at least one compound of the formula

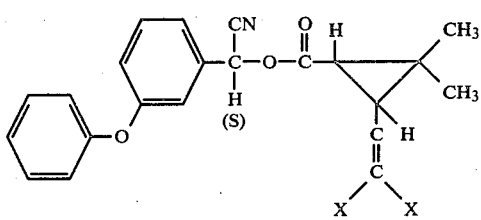

wherein X is selected from the group consisting of chlorine and bromine and the alcohol is the (S) structure and the acid has the cis or trans, racemic or optically active form. The compounds are usually applied by incorporation into the soil for combatting nematodes or by spraying the plants to be protected.

(S) α-cyano-3-phenoxy-benzyl 1R, cis 2,2-dimethyl-3-(2',2'-dichlorovinyl)-cyclopropane-1-carboxylate may be prepared as described in Belgium Pat. No. 853,867. The said compound may also be admixed with an equimolar or non-equimolar amount of the (R) α-cyano-3-phenoxy-benzyl ester of the same acid which is still within the scope of the inventions.

In the following examples there are described several preferred embodiments to illustrate the invention. However, it should be understood that the invention is not intended to be limited to the specific embodiments.

EXAMPLE 1

ACARICDE COMPOSITION

An emulsifiable concentrate was prepared containing 25 g of (S) α-cyano-3-phenoxy-benzyl 1R, cis 2,2-dimethyl-3-(2',2'-dibromovinyl)-cyclopropane-1-carboxylate, 6.4 g of Atlox 4851 (oxyethylene triglyceride with a sulfonate-acid index of 1.5), 3.2 g of Atlox 4855 (oxyethylene triglyceride with a sulfonate-acid No. of 3) and 65.4 g of xylene.

EXAMPLE 2

NEMATOCIDE COMPOSITION

An emulsifiable concentrate for treatment of nematodes was prepared containing 45% by weight of (S)α-cyano-3-phenoxy-benzyl 1R, cis 2,2-dimethyl-3-(2',2'-dibromovinyl)-cyclopropane-1-carboxylate, 6.4% by weight of Atlox 4851, 3.2% by weight of Atlox 4855 and 45.4% by weight of xylene.

A. ACARAICIDAL ACTIVITY

The acaricidal activity of (S) α-cyano-3-phenoxy-benzyl 1R, cis 2,2-dimethyl-3-(2',2'-dichlorovinyl)-cyclopropane-1-carboxylate (compound A) and (S) α-cyano-3-phenoxy-benzyl 1R, cis 2,2-dimethyl-3-(2',2'-dibromovinyl)-cyclopropane-1-carboxylate (compound B) was determined against Eotetranychus Carpini, a natural vine parasite. 4 elementary parcels containing 6 vine stocks each were used with one parcel serving as the non-treated control. The treatment was effected with a Van der Weij apparatus with a constant pressure at its limiting flow and reading were taken 3,8,14,30 and 45 days after treatment to count the number of acariens present on 15 leaves taken from each elementary parcel. Each leaf was mechanically brushed and the acariens were projected on to a glued plate and were counted with a binocular magnifying glass (mobile forms were counted). The results are reported in Table I.

TABLE I

| Compound | Doses g/hl | Readings in days | | | | | |
|---|---|---|---|---|---|---|---|
| | | 0 | 3 | 8 | 14 | 30 | 45 |
| A | 2.5 | 293 | 85 | 21 | 18 | 64 | 149 |
| | 5 | 320 | 96 | 26 | 18 | 21 | 74 |
| | 2.5 | 256 | 120 | 48 | 85 | 322 | 328 |
| B | 5 | 412 | 93 | 45 | 13 | 66 | 210 |
| | 10 | 280 | 66 | 16 | 16 | 21 | 50 |
| Control | 0 | 325 | 449 | 541 | 733 | 1429 | 1293 |

The results of Table I show that compounds A and B possess an interesting acaricidal activity against Eotetranychus Carpini on the vines.

B. ACARICIDAL ACTIVITY AGAINST PANONYCHUS ULMI

This study was effected with compound B against Panonychus Ulmi, a natural parasite for apple trees. The test was again effected on 4 elementary parcels, each containing 2 apple trees, with one untreated parcel serving as the control. The treatment was effected as above and readings were taken 3,8 and 15 days after treatment. The number of acariens was determined on 15 leaves from each parcel with each leaf being mechanically brushed so that the acariens fall on a glued plate and the number of mobile forms of acariens was read with a binocular magnifying glass. The results, expressed as a percentage of efficacy by the Abbot formula, are reported in Table II.

TABLE II

| Compound | Dose in g/hl | No. of acariens at start of test | % efficacy after days | | |
|---|---|---|---|---|---|
| | | | 3 | 8 | 15 |
| B | 1.25 | 1732 | 95 | 85 | 87 |
| | 2.5 | 1717 | 98 | 98 | 98 |
| Controls | 0 | 2252 | 1662* | 1685* | 1571* |

*For the controls, the number of live acariens per 15 leaves.

The results of Table II show that compound B has an interesting acaricidal activity against Panonychus Ulmi in apple trees.

C. NEMATOCIDAL ACTIVITY

The nematocidal activity of compound B was determined by introducing 500 larvae of Ditylenchus Myceliophagus into 10 ml of an aqueous solution containing varying concentrations of compound B. 24 hours after treatment, counting was effected with a binocular magnifying glass and the results, expressed as a percentage of efficacy compared to the untreated controls, is reported in Table III.

TABLE III

| Compound | Dose in mg/liter | % efficacy after 24 hours |
|---|---|---|
| B | 10 | 100% |

The rsults of Table III show that compound B has a good nematocidal activity against Ditylenchus Myceliophagus.

Various modifications of the compositions and methods of the invention may be made without departing from the spirit or scope thereof and it should be understood that the invention is intended to be limited only as defined in the appended claims.

We claim:

1. A method of combatting vegetable nematodes comprising contacting the vegetable nematodes with a nematocidally effective amount of at least one compound of the formula

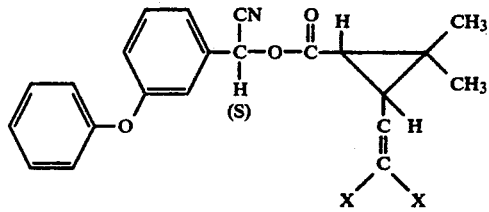

wherein X is selected from the group consisting of chlorine and bromine and the alcohol is the (S) structure and the acid has the cis or trans, racemic or optically active form.

2. The method of claim 1 wherein the compound is (S) α-cyano-3-phenoxy-benzyl 1R, cis 2,2-dimethyl-3-(2',2'-dichlorovinyl)-cyclopropane-1-carboxylate.

3. The method of claim 1 wherein the compound is (S) α-cyano-3-phenoxy-benzyl 1R, cis 2,2-dimethyl-3-(2',2'-dibromovinyl)-cyclopropane-1-carboxylate.

* * * * *